United States Patent [19]

Samuelsson

[11] Patent Number: 6,024,732
[45] Date of Patent: Feb. 15, 2000

[54] PACKAGING FOR A SANITARY NAPKIN OF LIKE ARTICLE

[75] Inventor: Ann Samuelsson, Lindome, Sweden

[73] Assignee: SCA Molnlycke AB, Gothenberg, Sweden

[21] Appl. No.: 09/029,544

[22] PCT Filed: Sep. 6, 1996

[86] PCT No.: PCT/SE96/01111

§ 371 Date: Mar. 5, 1998

§ 102(e) Date: Mar. 5, 1998

[87] PCT Pub. No.: WO97/12572

PCT Pub. Date: Apr. 10, 1997

[30] Foreign Application Priority Data

Oct. 2, 1995 [SE] Sweden ................................. 9503401

[51] Int. Cl.[7] ....................................................... A61F 13/15
[52] U.S. Cl. ........................... 604/390; 604/387; 604/389; 206/438
[58] Field of Search ................................ 604/385.1, 387, 604/389, 390; 206/438, 440

[56] References Cited

U.S. PATENT DOCUMENTS

| H1454 | 6/1995 | Cucuzza et al. | 604/390 |
|---|---|---|---|
| 3,973,567 | 8/1976 | Srinivasan et al. | 604/390 |
| 5,342,339 | 8/1994 | Carpenter et al. | 604/389 |
| 5,413,568 | 5/1995 | Roach et al. | 604/390 |
| 5,484,636 | 1/1996 | Berg et al. | 604/390 |
| 5,569,228 | 10/1996 | Nyrd et al. | 604/387 |
| 5,569,230 | 10/1996 | Fisher et al. | 604/387 |
| 5,683,377 | 11/1997 | Mizutani | 604/387 |
| 5,792,131 | 8/1998 | Miztani | 604/390 |

FOREIGN PATENT DOCUMENTS

| 0 357 000 | 3/1990 | European Pat. Off. . |
| 0 357 298 | 3/1990 | European Pat. Off. . |
| 2 273 279 | 6/1994 | United Kingdom . |

Primary Examiner—M. Polutta
Attorney, Agent, or Firm—Young & Thompson

[57] ABSTRACT

A packaging for a sanitary napkin (1) or like article, wherein the outer surface of the sanitary napkin is at least partially adhesive and the napkin is folded so that the adhesive outer surface thereof faces towards the packaging material. The packaging material presents a relatively small surface area for contact with the outer surface of the sanitary napkin.

5 Claims, 1 Drawing Sheet

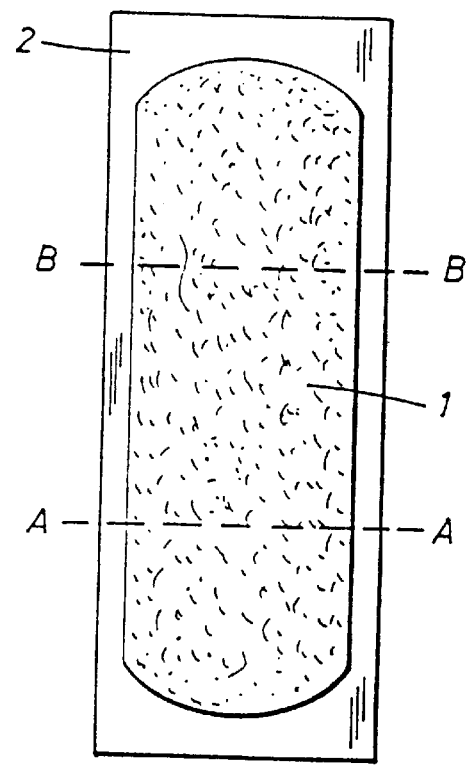
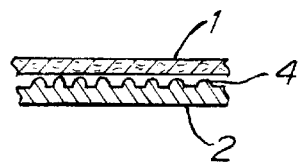
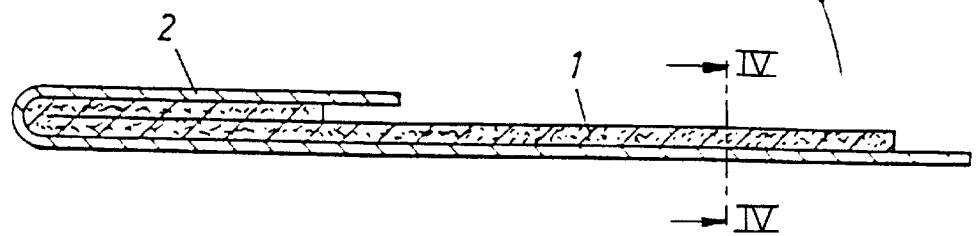
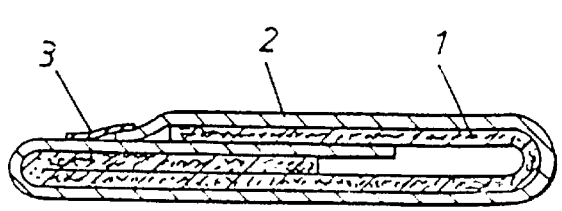

PACKAGING FOR A SANITARY NAPKIN OF LIKE ARTICLE

FIELD OF THE INVENTION

The present invention relates to packaging material for a sanitary napkin or like article wherein the sanitary napkin has an at least partially adhesive outer service and is folded so that this adhesive surface faces towards the packaging material.

BACKGROUND OF THE INVENTION

Sanitary napkins and panty protectors are often packaged in a folded state in units for one-time use only, so that they can be carried hygienically and unnoticed for later use in a handbag for instance. The outer surface of a sanitary napkin or a panty protector is coated at least partially with an adhesive, so that the napkin or panty protector can be fastened to the inside of a pair of panties. To avoid the coating preventing the package from being opened or to avoid the coating being destroyed by the packaging material, it is normal practice to protect the adhesive coating with a release paper or release foil. An alternative method of solving this problem is to coat the packaging material with a release agent, for instance with a siliconized resin. As an example of this method EP-A1-0 357 000 is referred to. However, both of the solutions are relatively expensive.

OBJECTS OF THE INVENTION

One object of the present invention is to provide a packaging material for a single sanitary napkin package or a single panty intended for one-time use only with which no release agent is required and with which the adhesive coating on the sanitary napkin or the panty protector need not be protected against destruction by the packaging material.

SUMMARY OF THE INVENTION

These objects are achieved in accordance with the invention with packaging material of the kind defined in the introduction and characterized in that the packaging material, on the surface facing the adhesive outer surface of the sanitary napkin, is provided with a multiple of projections in order to present a small surface area for contact with the outer surface of the sanitary napkin.

According to a first embodiment of the invention, the packaging material is a melt-bonded patterned nonwoven material.

In alternative embodiments of the invention, packaging material is comprised respectively of a laminate of plastic film and nonwoven material, plastic film which is covered on one side with small projections, or a plastic film which includes on one side longitudinally extending and transversely extending ribs which together form a net structure.

BRIEF DESCRIPTION OF THE DRAWINGS

The invention will now be described with reference to the accompanying drawings, in which FIG. 1 is a view from above of a sanitary napkin placed on top of a packaging blank;

FIG. 2 is a cross-sectional view showing a first folding step in the manufacture of a single-article package with a starting point from the packaging blank in FIG. 1; and FIG. 3 is a cross-sectional view of a single-article package in accordance with a first embodiment of the invention.

FIG. 4 is a cross-sectional view taken along line IV—IV of FIG. 2.

DESCRIPTION OF THE PREFERRED EMBODIMENTS

FIG. 1 shows a sanitary napkin 1 placed on top of a sheet 2 of packaging material. The side of the sanitary napkin 1 distal from the viewer of FIG. 1 is coated with an adhesive so that the napkin can be fastened to a pair of panties from the inside, and thus adheres to the inner surface of the sheet 2. In order to provide a single-pack sanitary napkin with a starting point from the configuration shown in FIG. 1, the unit consisting of the napkin 1 and the sheet 2 is first folded about the contemplated fold line A—A shown in broken line in FIG. 1, so as to give the unit 1, 2 the configuration shown in FIG. 2. The unit 1, 2 is then folded around the contemplated fold line B—B shown in a broken line in FIG. 1, to obtain the package configuration shown in FIG. 3. The sanitary napkin is held together in this folded state with the aid of a fastener tape 3, which fastens that part of the sheet 2 which has been folded around the line B—B to the part that was earlier folded inwards about the line A—A. The mutually facing parts of the folded side edges of the sheet 2 are then fastened together, for instance by welding or gluing.

When wishing to open the single-article package, the side-edges of the sheet 2 are broken away and the unit 1, 2 folded out to the state shown in FIG. 1. The sanitary napkin 1 is then loosened from the sheet 2. In order to achieve this without impairing the ability of the sanitary napkin to fasten to a pair of panties, the sheet 2 must adhere to the glue-coated outside of the sanitary napkin with only a slight force. This is achieved in accordance with the invention with a sheet 2 which presents a small surface area for contact with the packaged article, i.e. the sheet has an irregular surface which includes a multiple of projections 4 that abut the sanitary napkin and distance the remainder of the inner surface of the sheet 2 from the outer surface of the sanitary napkin. These projections 4 may have any suitable form, provided that the sum of the projection abutment surfaces with the sanitary napkin remains small in relation to the total area of the inner surface of the sheet 2.

It has surprisingly been found that nonwoven material, preferably a melt-bonded nonwoven material, well bonded in a pattern, can be used without greatly impairing the ability of the sanitary napkin to fasten securely to a pair of panties. This is because even though some fibres fasten to the adhesive layer on the sanitary napkin, the major part of the adhesive layer or layers will be free from fibres. Such nonwoven material is bonded by passing the material between a smooth roll and a pattern roll, such as to produce a patterned surface which is essentially free from upstanding fibre ends.

The sheet 2 may alternatively consist of a plastic film/nonwoven laminate, this laminate being particularly suitable when an open nonwoven structure is used. Plastic film provided with projections may also be used as packaging material, for instance plastic film having a net structure on one side thereof.

The sanitary napkin 1 shown in the Figures is coated with adhesive over essentially the whole of its outer surface, which makes the napkin particularly suitable for packaging in a single-article package according to the invention. However, the invention can also be applied with sanitary napkins whose outer surfaces include solely one or more glue strings, without greatly impairing the function of these strings as the package is opened.

It will be understood that the described and illustrated embodiment can be modified within the scope of the invention, particularly with regard to the form and construction of the sanitary napkin. Folding of the package unit and the packaging may be different to that shown. For instance, the sanitary napkin may be folded in its package so that it can be removed therefrom without needing to break open the side joins of the package. Alternatively, the package may be folded in a manner which removes the need for side joins. The invention is therefore only restricted by the content of the following claims.

I claim:

1. A packaged sanitary napkin comprising:

a sanitary napkin having an at least partially adhesive outer surface;

a sheet of packing material wrapped around the sanitary napkin and having an inner surface facing the adhesive outer surface of the sanitary napkin, the sanitary napkin being folded so that the adhesive outer surface faces towards the inner surface;

said inner surface being free from release coating and including a plurality of projection abutment surfaces which abut the sanitary napkin and distance the remainder of the inner surface of the sheet from the adhesive outer surface; and wherein the sum of the projection abutment surfaces is small in relation to the total surface area of the packaging material facing the sanitary napkin, such that a major part of adhesive on the adhesive outer surface will remain intact after removal of the packaging material.

2. The packaged sanitary napkin according to claim 1, wherein the packaging material is a melt-bonded patterned nonwoven material.

3. The packaged sanitary napkin according to claim 1, wherein the packaging material is a laminate consisting of plastic film and a nonwoven material.

4. The packaged sanitary napkin according to claim 1, wherein the packaging material is comprised of plastic film whose one side is covered with small projections.

5. The packaged sanitary napkin according to claim 1, wherein the packaging material is comprised of plastic film whose one side includes longitudinally extending and transversely extending ribs which together form a net structure.

* * * * *